US011281027B2

(12) United States Patent
Poteet

(10) Patent No.: US 11,281,027 B2
(45) Date of Patent: Mar. 22, 2022

(54) EYEGLASSES AND METHODS OF INACTIVATING A VIRUS WITH ULTRAVIOLET LIGHT

(71) Applicant: Everett Ewell Poteet, Royal Oak, MI (US)

(72) Inventor: Everett Ewell Poteet, Royal Oak, MI (US)

(*) Notice: Subject to any disclaimer, the term of this patent is extended or adjusted under 35 U.S.C. 154(b) by 0 days.

(21) Appl. No.: 17/242,744

(22) Filed: Apr. 28, 2021

(65) Prior Publication Data

US 2021/0356771 A1 Nov. 18, 2021

Related U.S. Application Data

(60) Provisional application No. 63/101,695, filed on May 12, 2020.

(51) Int. Cl.
| | | |
|---|---|---|
| *G02C 11/04* | (2006.01) | |
| *A61L 9/20* | (2006.01) | |
| *B08B 7/00* | (2006.01) | |
| *A61L 9/00* | (2006.01) | |

(52) U.S. Cl.
CPC ............ *G02C 11/04* (2013.01); *A61L 9/00* (2013.01); *A61L 9/20* (2013.01); *B08B 7/0057* (2013.01); *A61L 2209/00* (2013.01); *A61L 2209/10* (2013.01); *A61L 2209/12* (2013.01)

(58) Field of Classification Search
CPC ... G02C 11/04; A61L 9/00; A61L 9/20; A61L 2209/00; A61L 2209/10; A61L 2209/12; B08B 7/0057
USPC .................................. 250/455.11; 422/186.3
See application file for complete search history.

(56) References Cited

U.S. PATENT DOCUMENTS

| 11,033,060 B1* | 6/2021 | Yelken ................... A41D 13/11 |
| 2013/0057849 A1 | 3/2013 | Yeh |
| 2017/0075146 A1* | 3/2017 | Nishimura et al. ...... G02C 7/16 |
| 2019/0160305 A1 | 5/2019 | Randers-Pehrson et al. |

FOREIGN PATENT DOCUMENTS

| CN | 210323613 U | 4/2020 |
| CN | 210384624 U | 4/2020 |

OTHER PUBLICATIONS

Hiroshima University, "A Safer UV Light Effectively Kills Virus Causing Covid-19". Science Daily, Sep. 17, 2020, 4 pgs. <www.sciencedaily.com/releases/2020/09/200917105345.htm>.
"Kobe University and Ushio Find 222nm UVC Radiation Safe for Human Skin", LEDinside, Apr. 10, 2020, 3 pgs. https://www.ledinside.com/new/2020/4/222nm_uve_harmless.

* cited by examiner

*Primary Examiner* — Kiet T Nguyen
(74) *Attorney, Agent, or Firm* — Young Basile Hanlon & MacFarlane, P.C.

(57) ABSTRACT

An eyeglass device for inactivating a pathogen includes an eyeglass frame connectable with a face of a person and a pair of lenses connected with the eyeglass frame. The pair of lenses includes a composition that blocks some wavelengths of beams of ultraviolet light. The eyeglass device further includes a light affixed to the eyeglass frame and that emits an ultraviolet light beam having a wavelength of about 205 nm to about 225 nm and does not emit an ultraviolet light beam having a wavelength of about 254 nm. Methods of inactivating a pathogen are also described.

20 Claims, 7 Drawing Sheets

EYEGLASSES AND METHODS OF INACTIVATING A VIRUS WITH ULTRAVIOLET LIGHT

TECHNICAL FIELD

This disclosure relates generally to eyewear, and more particularly to an eyeglass device such as eyeglasses, that emits ultraviolet light so that a pathogen can be safely inactivated in front of a face of a person and methods of use thereof.

BACKGROUND

Infectious diseases stemming from pathogens that are airborne present particular challenges in everyday life, as the pathogens are often in aerosol form that are easily inhaled or exhaled. In addition to these pathogens being easily inhaled or exhaled, the aerosol form can be caught in the eyes or lips and, subsequently, can cause an undesirable infection that is easily spread to other humans. This problem is exacerbated more because so many people live and interact in highly populated and enclosed areas, like hospitals, office buildings, malls, grocery stores, gyms, or the like.

At times, pathogens emerge that have very high infection rates, which may trigger a pandemic situation were additional personal protection equipment ("PPE") is desired to avoid becoming infected or mitigating spread of the pathogen. In the past, healthcare workers and lay people have worn PPE, like masks and gaiters, and, in combination, have vigorously applied disinfectants of various sorts to the surfaces that come in contact with people and hands of people.

BRIEF SUMMARY

Masks are not 100 percent effective at preventing the spread of pathogens in aerosol form to and from the mouth and/or nose, and surface disinfectants do not inactivate pathogens in aerosol form. Thus, there is a need for devices and techniques that can provide methods of inactivating pathogens in an aerosol form so that inhalation or transmission of active pathogens is prevented or further limited.

An aspect of the teachings herein is an eyeglass device for inactivating a pathogen that includes a frame connectable with a face of a person. The eyeglass device further includes one or more lenses connected with the frame and a light emission source connected to the frame. The light emission source emits an ultraviolet light beam having a wavelength of about 190 nm to about 225 nm.

Another aspect of the teachings herein is a method of inactivating a pathogen that includes securing an eyeglass device connected with a light emission source at a frame of the eyeglass device. Eyes of a person are covered by one or more lenses of the frame. The light emission source directs ultraviolet light away from a face of the person. The method further includes activating the light emission source of the eyeglass device so that the ultraviolet light is emitted. The ultraviolet light has a wavelength between about 190 nm and about 225 nm. The method further includes inactivating the pathogen having a form of an aerosol droplet that is floating in front of the face of the person.

Still another aspect of the teachings herein are eyeglasses for inactivating a pathogen that include an eyeglass frame connectable with a face of a person. The eyeglasses further include a pair of lenses connected with the eyeglass frame. The pair of lenses include a composition that blocks some wavelengths of beams of ultraviolet light. The eyeglasses further include a light affixed to the eyeglass frame, and the light emits an ultraviolet light beam having a wavelength of about 205 nm to about 225 nm. The light does not emit an ultraviolet light beam having a wavelength of about 254 nm.

Accordingly, the eyewear, eyeglass devices, eyeglasses, and methods herein inactivate a pathogen having an aerosol form floating near highly infection-able areas, like the eyes, nose, and mouth, by using beams of ultraviolet light at safe wavelengths.

DETAILED DESCRIPTION

As used herein, a pathogen means any organism that can have a form of an aerosol droplet and can cause an infection in a person, such as a virus, bacteria, fungi, or any other infections item that can have an aerosol form. "Personal protection equipment" or "PPE" includes, but is not limited to, face shields, gloves, goggles and glasses, gowns, head covers, masks, respirators, and shoe covers. As used herein, inactive or inactivating means causing the pathogen to denature, deform, and/or corrupt so that the pathogen can no longer infect a person. A light(s) may be described as a light emission source, a light source, lamp, torch, or any combination thereof.

In general, the present disclosure provides an apparatus (e.g., eyewear such as an eyeglass device or eyeglasses) and methods of using the apparatus to prevent infection and transmission of a pathogen having an aerosol form. The apparatus includes a light emission source that emits a beam of ultraviolet light in front of the face of a person to inactivate one or more pathogens that are floating in an aerosol form in the air. Beams of ultraviolet light at a wavelength of about 254 nm are known to inactivate pathogens and, also, cause damage to human epithelial tissue. On the other hand, the beam of ultraviolet light used in the present disclosure is configured to emit at a wavelength of about 190 to about 225 nm so that the pathogen can be denatured, and the beam of ultraviolet light at the wavelength of about 190 nm to about 225 nm does not damage tissue of a person. To mitigate possible long-term irritation of the eyes from the beam of ultraviolet light, a composition sufficient to block the ultraviolet light at all or only some wavelengths that are emitted from the light emission source is included to protect the eyes of a person. By either constantly or intermittently emitting the beam of ultraviolet light, the apparatus can be worn to cover the eye(s) of a person and eliminate the threat of transmitting or contracting a disease from an airborne pathogen because the pathogens are inactivated upon being caught within the beam of ultraviolet light.

Figure 1:
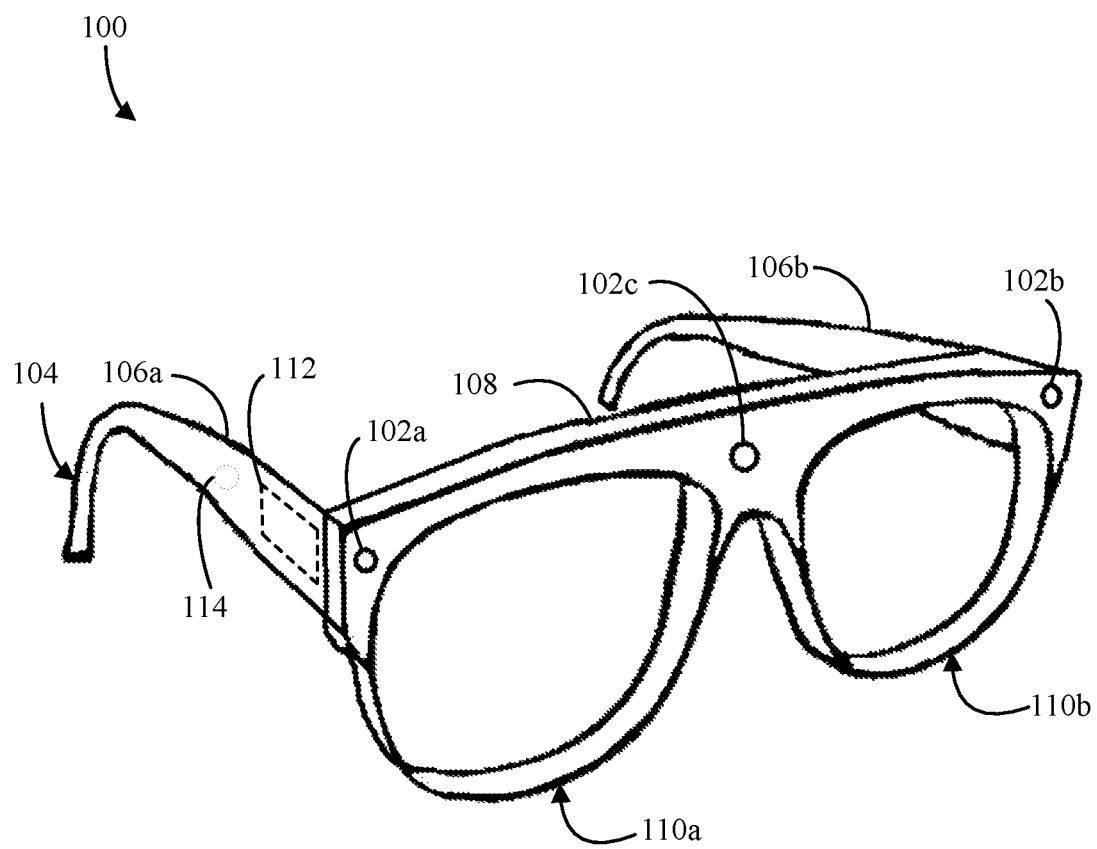
FIG. 1 is a perspective view of an eyeglass device for inactivating a virus or bacteria.

FIG. 1 is a perspective view of eyewear or an eyeglass device 100, more specifically eyeglasses in this example, for inactivating a pathogen according to an example of the teachings herein. The eyeglass device 100 includes light emission sources 102a, 102b, 102c that are affixed to a frame 104 of the eyeglass device 100. In this example, two of the light emission sources 102a, 102b are associated with temples 106a, 106b of the frame 104, and the other light emission source 102c is associated with a bridge 108 of the frame 104. At a front surface of the frame 104, lens rims 110a, 110b having a pair of lenses that are transparent are affixed to the frame 104. The pair of lenses are arranged to cover the eyes of a person.

Figure 2:
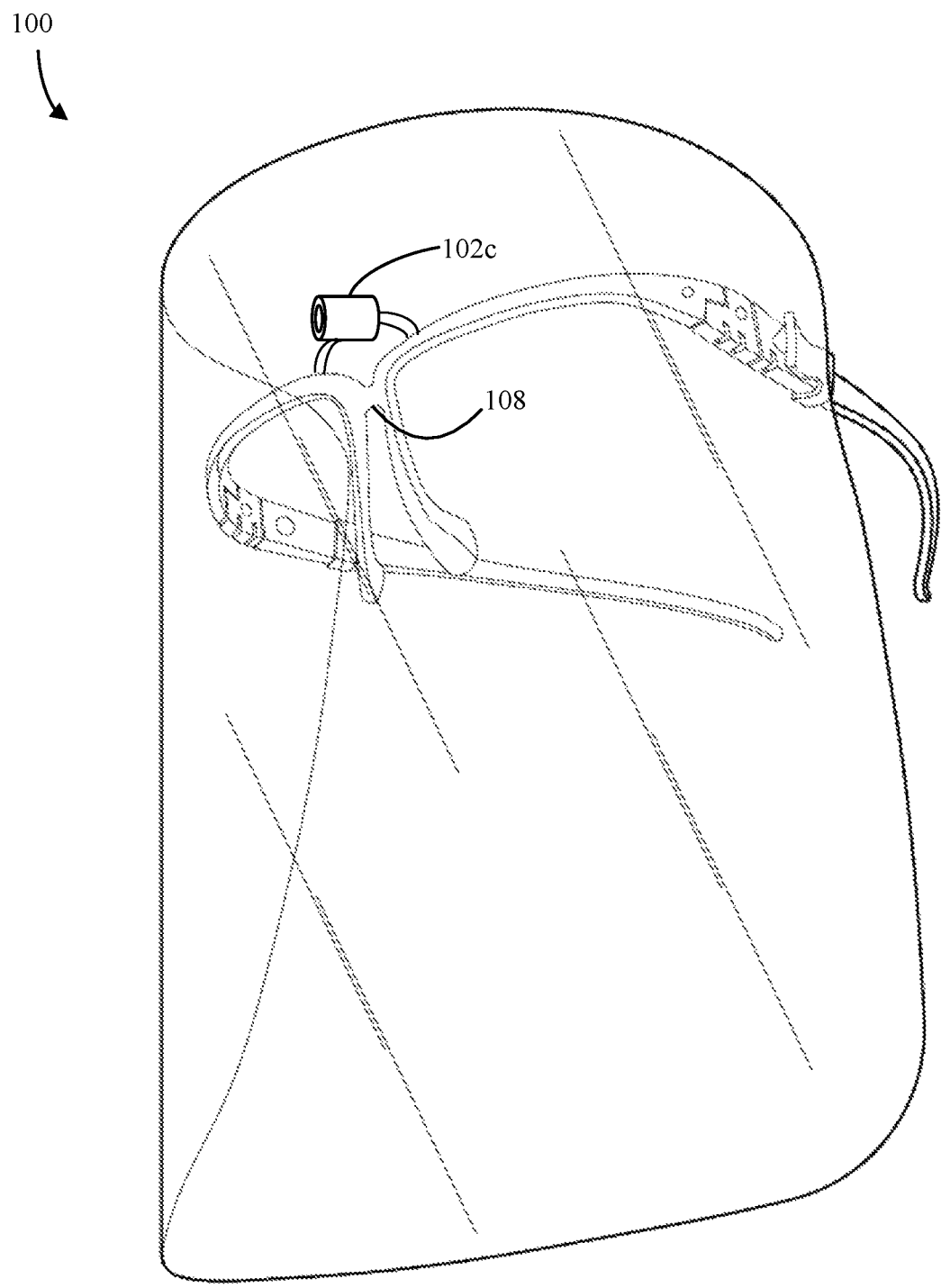
FIG. 2 is a perspective view of a face shield for inactivating a virus or a bacteria.
Figure 3:
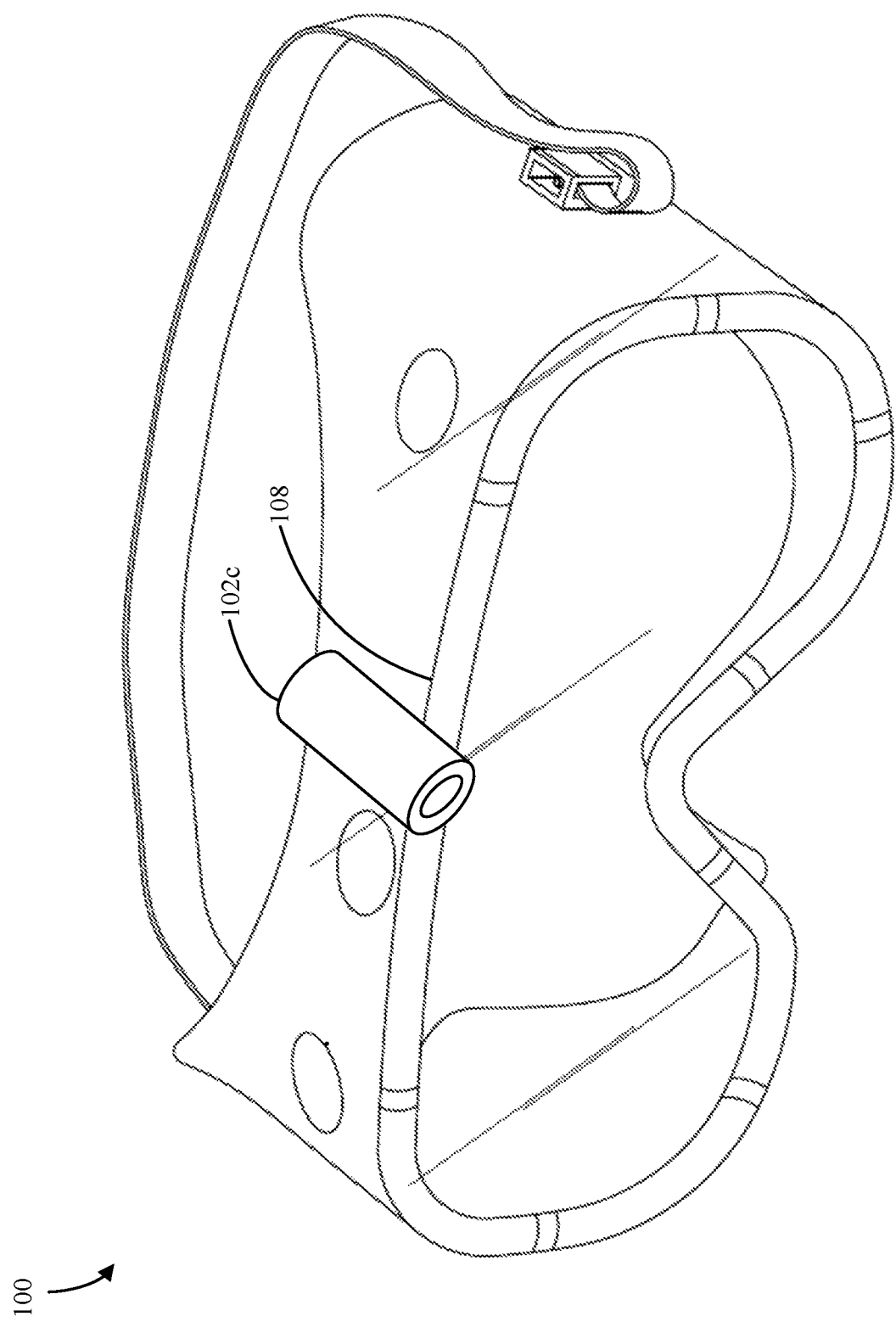
FIG. 3 is a perspective view of goggles for inactivating a virus or a bacteria.

In FIG. 1, the eyewear or eyeglass device 100 is eyeglasses that allow a person to easily wear the eyeglass device 100 in everyday activities. In other examples, the eyeglass device 100 is a face shield (e.g., as shown in FIG. 2), goggles (e.g., as shown in FIG. 3), or any other head mountable device that can be worn on the head and covers the eye(s) of a person. In some examples, the eyeglass device 100 includes a single lens (not shown), such as a face shield or visor, to reduce exposure of the eyes by not having a gap between the lenses proximate to the nose. In other examples, the eyeglass device 100 includes a strap or a circular plastic or metal mount that encircles a head of a person instead of the temples 106a, 106b so that the eyeglass device 100 has improved securement to the head of a person. In some examples, the frame 104 is integrated with straps or clips that secure the eyeglass device 100 to the head of a person without covering the top of the head of a person.

Figure 4:
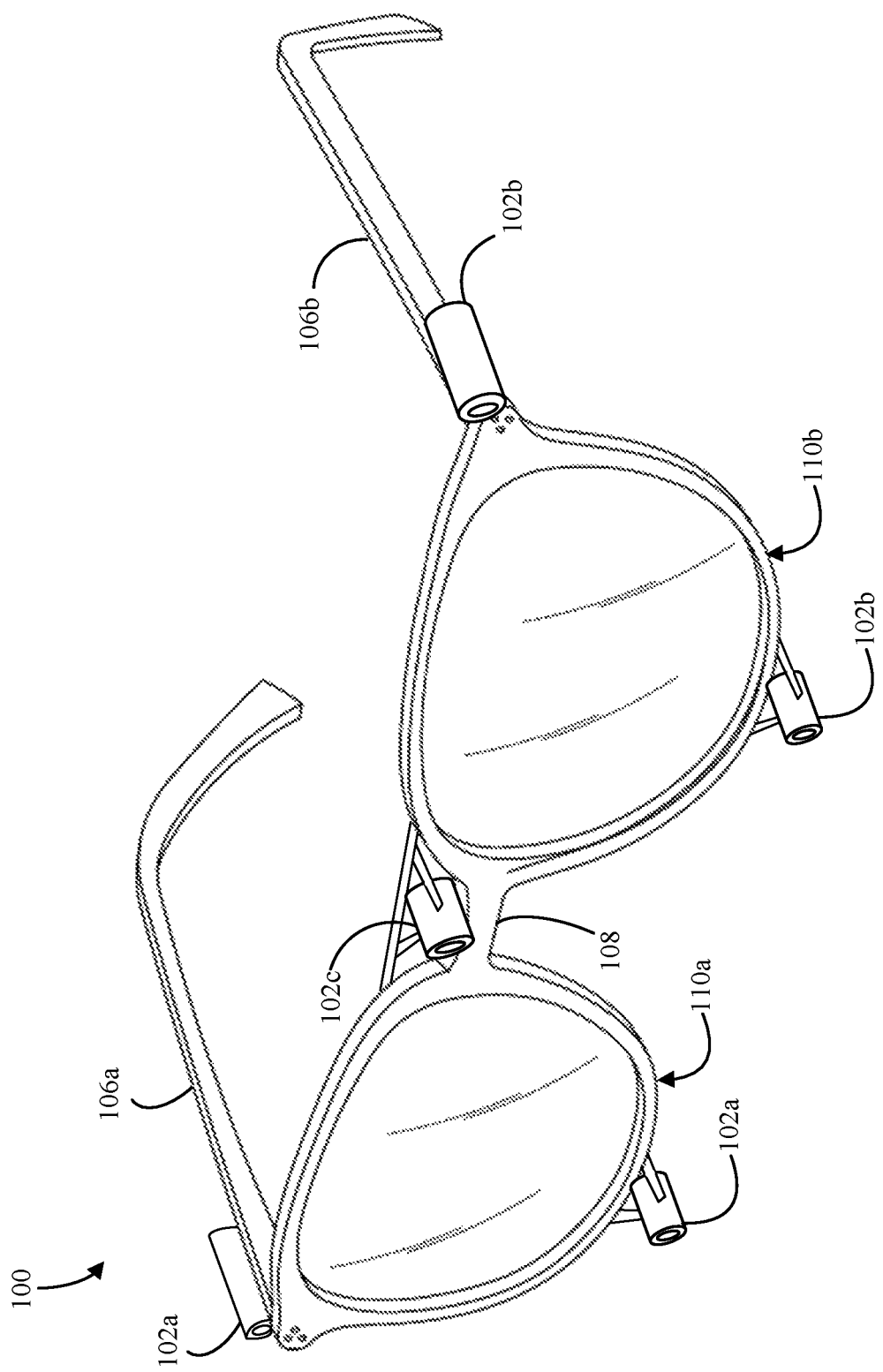
FIG. 4 is a perspective view of an eyeglass device for inactivating a virus or bacteria.

The temples 106a, 106b are rotatably connected with the frame 104, and the light emission sources 102a, 102b extend from the temples 106a, 106b by being connected with a power source 112 housed in one or both of the temples 106a, 106b (shown in the temple 106a). As shown, the light emission source 102c is integrated with the bridge 108 of the frame 104 so that the beam of ultraviolet light can be emitted in a centralized position above a nose of a person. In other examples, the light emission source 102c may be positioned above either or both of the lens rims 110a, 110b so that two light emission sources (e.g., FIG. 4) are positioned in a centralized fashion. In some examples, the light emission source 102c is not integrated with the frame 104, and the light emission source 102c may be affixed to an outer surface of the frame 104 proximate to the bridge 108, for example, above the bridge 108 (e.g., FIGS. 2-4) and/or lens rims 110a, 110b or below the bridge 108 and/or the lens rims 110a, 110b (e.g., FIG. 4) so that the light emission source 102c may rest on a cheek or nose of a person.

The power source 112 may be, or include, a battery. Although the light emission sources 102a, 102b are shown as positioned on a front surface of the frame 104, the light emission sources 102a, 102b may be affixed to an outer side surface of the temples 106a, 106b with ends of the light emission sources 102a, 102b positioned behind the front surface of the frame 104 and extending perpendicularly from the temples 106a, 106b so that, when activated, the light emission sources 102a, 102b emit a beam that is partially blocked from reaching eyes of a person by the temples 106a, 106b. The power source 112 is shown completely integrated with the temples 106a, 106b so that a bulge from a side surface of the eyeglass device 100 is avoided. In other examples, the power source 112 may be positioned on the outside of the temples 106a, 106b, integrated with the lens rims 110a, 110b or bridge 108, or integrated or positioned anywhere else on the frame 114 that allows the light emission sources 102a, 102b, 102c to be electrically coupled with the power source 112.

While the power source 112 is housed in the temple 106, in other implementations, the power source may be integrated with the bridge 108 or the lens rims 110a, 110b. The power source 112 functions to provide (e.g., a direct) current to the light emission sources 102a, 102b, 102c through suitable electrical connections. The power source 112 may turned on and off using a switch 114. As shown, the switch 114 extends into the interior of the temple 106, but the optional switch 114 may be placed at other locations of the eyeglass device 100 so that a person wearing the eyeglass device 100 can easily control the output of the beam of ultraviolet light from the light emission sources 102a, 102b, 102c.

The power source 112 may include switching circuitry electrically coupled between a battery or other power supply and the light emission sources, such as the light emission sources 102a, 102b, 102c. In addition to controlling whether the light emission sources 102a, 102b, 102c are on or off, the switching circuitry may be programed to allow electricity to flow to the light emission sources 102a, 102b, 102c to generate a lower, intermediate, or higher emission output so that varying degrees of emission strength of the beams of ultraviolet light are output. In still other examples, the switching circuitry may be programmed to control whether the beam of ultraviolet light is emitted in an intermittent fashion. In still other examples, the switching circuitry may allow emission of the beams of ultraviolet light for a period of time, such as between about 10 seconds and about 30 minutes, once the switch is activated so that a person can avoid leaving the light emission sources 102a, 102b, 102c on for too long and draining battery life. Any or all of these modes may be controlled or activated by tapping, switching, or pressing a component (e.g., a button or the like) positioned on an external surface of the eyeglass device 100, such as the switch 114. That is, for example, the switch 114 may be integrated with the switching circuitry to control whether the light emission source 102a, 102b, 102c is in any particular mode, such as on/off, low/intermediate/high emission strength, intermittent flashing, and/or timed emission, e.g., through sequential pressing of the switch 114.

The power source 112 described herein may include any power source sufficient to power the light emission sources 102a, 102b, 102c that emit a wavelength of about 190 nm to about 225 nm. When a battery is used, the battery may be easily replaceable or may be a fixed battery that is charged by a standard wall plug-in charger or any type of wireless recharging device. In some examples, the battery may be charged by solar charging devices positioned anywhere on the frame 104 of the eyeglass device 100 so that the person using the eyeglass device 100 can charge the battery while traveling between separately positioned buildings.

Figure 5:
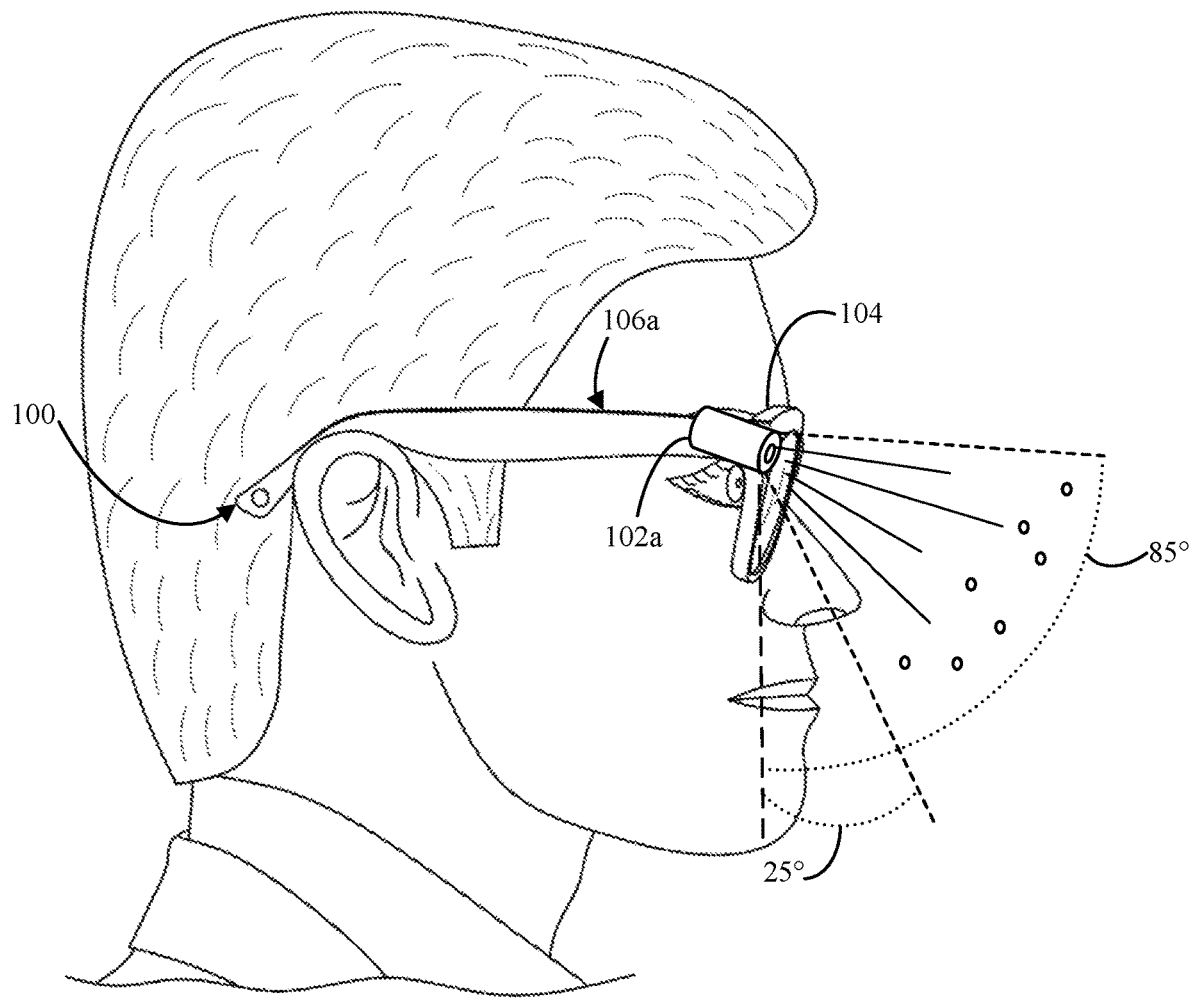
FIG. 5 is a side view showing emission of light from a light source at a downward angle of about 85 degrees to about 25 degrees.
Figure 6:
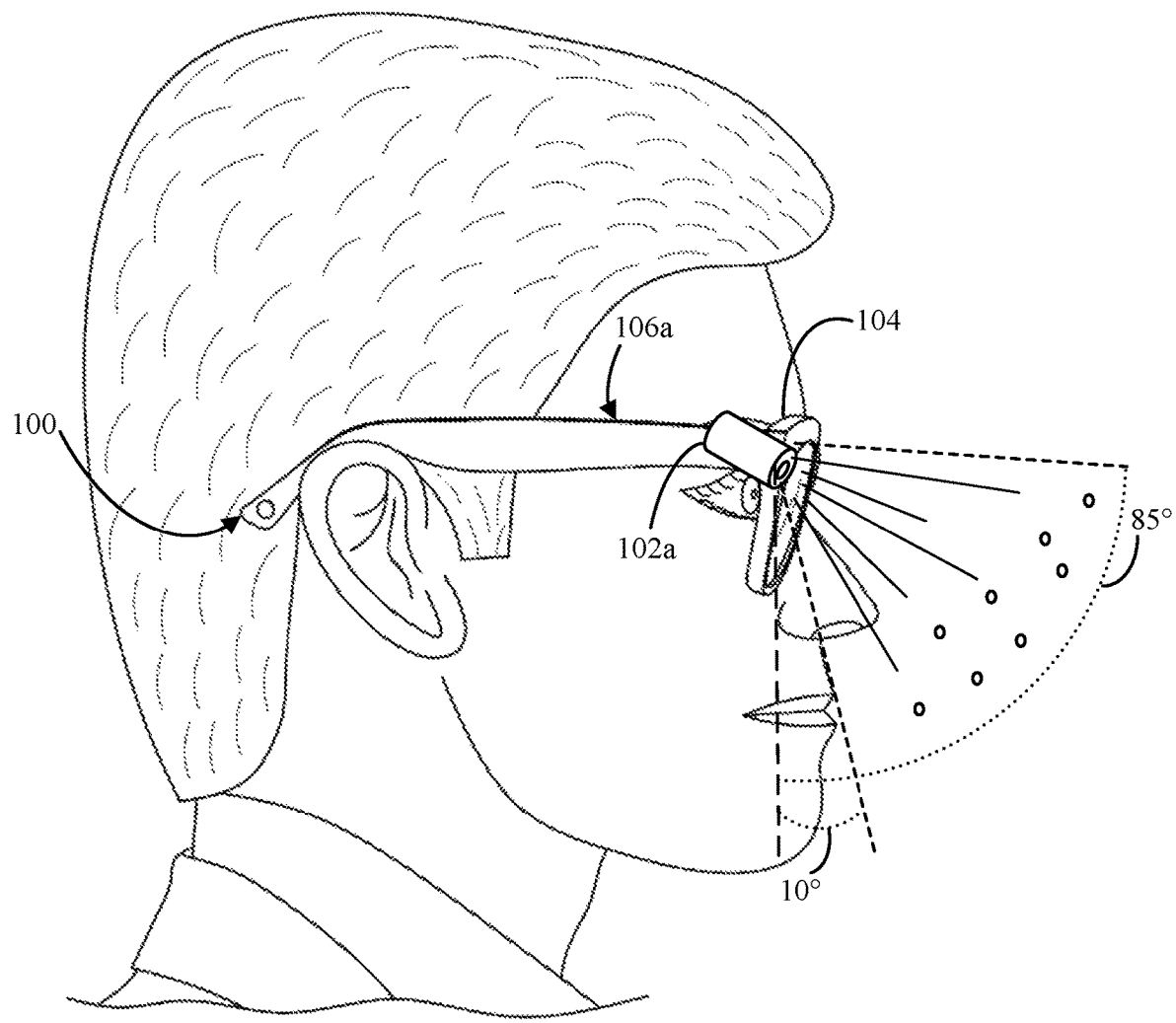
FIG. 6 is a side view showing emission of light from a light source at a downward angle of about 85 degrees to about 10 degrees.
Figure 7:
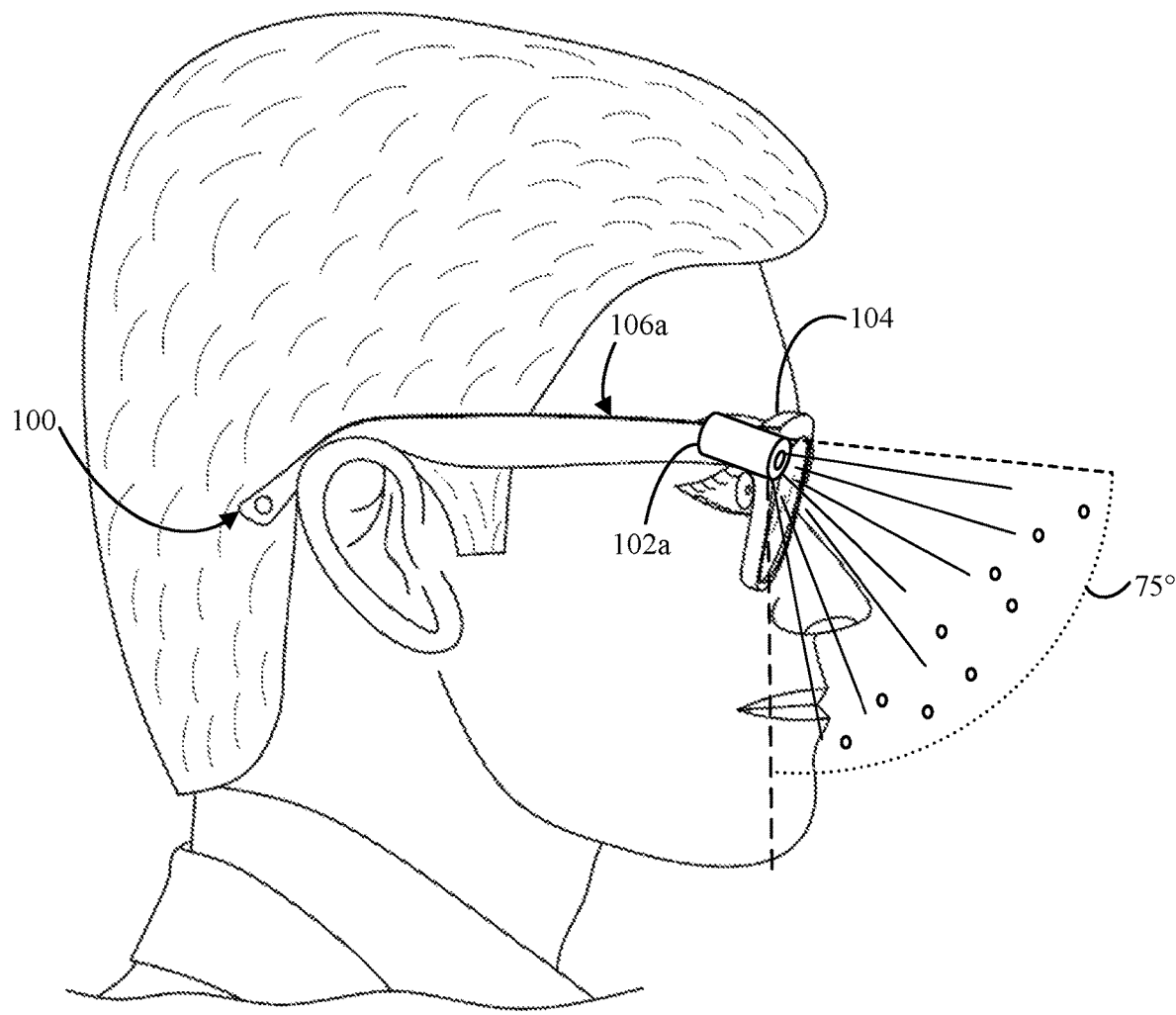
FIG. 7 is a side view showing emission of light from a light source at a downward angle of below about 75 degrees.

In FIG. 1, the light emission sources 102a, 102b, 102c are integrated with the frame 104 so that a beam of ultraviolet light is emitted at a generally perpendicular angle (i.e., about 90 degrees), relative to the outside surface of the frame 104. The light emission sources 102a, 102b, 102c may be integrated or affixed to the frame 104 at an angle so that the beams of ultraviolet light can optimally inactivate pathogens floating in front of a face of a person. The light emission sources 102a, 102b, 102c may be integrated or affixed at any angle sufficient to cover the space in front of the eyes, nose, and/or mouth of a person. The light emission sources 102a, 102b, 102c may be integrated or affixed at a generally downward angle so that the light is directed to cover the eyes, the nose, the mouth, or any combination thereof. For example, the downward angle relative to a horizontal plane passing through the head and outside surface of the frame 104 may be about 85 degrees or less, about 75 degrees or less, about 65 degrees or less, or about 55 degrees or less. The downward angle may be about 10 degrees or more, about 20 degrees or more, about 30 degrees or more, or about 40 degrees or more. Some examples of the resulting ranges of downward angles are shown in FIGS. 5-7. The light emission sources 102a, 102b, 102c may be positioned so that the beam of ultraviolet light does not shine into another person's eyes.

The lenses integrated with the lens rims 110a, 110b may be any composition that allows a person to see through the lenses. For example, the lenses may simply be transparent glass, transparent plastic, or both. In other examples, the lenses may contain a composition or coating that sufficiently blocks ultraviolet light that is damaging to the eyes of a person. The composition or coating may block all ultraviolet light or simply a range, such as a wavelength between about 100 and about 400 nm or any smaller range within 100 nm and 400 nm. The composition or coating may include a paint, a polymer, a mineral, or any combination thereof to block ultraviolet light along any desired range, such as 190 nm to about 225 nm, or at a specific target wavelength, such as any wavelength shorter or longer than 222 nm. In some examples, a two walled system (not shown) is used to block ultraviolet light, where two walls of glass or plastic are sealed together with an amount of a gas sealed between the two walls so that the gas blocks or deflects any desired range of ultraviolet light.

The light emission sources 102a, 102b, 102c may be composed of any material, compound, element, or component sufficient to emit an ultraviolet light at a wavelength between 190 nm and 225 nm. The material, compound, element, or component may be chosen so that the peak wavelength of ultraviolet light is about 207 nm, 222 nm, or both. The ultraviolet light may have a peak wavelength at about 207 nm, 222 nm, or both so that the pathogen is inactivated and human tissue is not damaged. For example, the light emission sources 102a, 102b, 102c may include krypton-bromine, krypton-chlorine, or both so that the peak of the ultraviolet light wavelength is about 207 nm, 222 nm, or both. Any other material, compound, element, or component could be chosen to be used in the light emission sources 102a, 102b, 102c, and any other component may be used in combination with the light emission sources 102a, 102b, 102c as a filter within the light emission sources 102a, 102b, 102c to remove any undesirable ultraviolet light wavelengths, such as the wavelength of 254 nm or other damaging or undesired wavelengths. Desirably, the beam of ultraviolet light may be invisible to the naked eye and visible light is excluded so that pathogens are inactivated and other persons around the person wearing the eyeglass device 100 are not bothered or irritated by the beam of ultraviolet light. Although less desirable, in other examples, the beam of ultraviolet light may be visible to the naked eye by having a beam of light that includes both ultraviolet light, visible light, and/or other wavelengths of light, so long as the eyes and/or skin of a person are not damaged from exposure of the light.

The strength of the beam of ultraviolet light functions to inactive pathogens a predetermined distance from the front of the face of the person. The beam of ultraviolet light may be sufficiently strong to catch a pathogen in the beam and inactivate the pathogen instantly or over a period of time, such as in 1 to 5 seconds. The beam of ultraviolet light may be sufficiently strong to emit energy a predetermined distance from the light emission sources 102a, 102b, 102c in front of the face of a person to inactivate the pathogen. The predetermined distance may be about 1 meter or less, about 0.75 meters or less, or about 0.5 meters or less. The predetermined distance may be about 0.2 meters or more, about 0.3 meters or more, or about 0.4 meters or more. The beam may be strong enough to inactivate pathogens on a surface that is spaced a distance from the person, such as a counter or table. In other examples, the beam may be strong enough to inactivate pathogens on the hands or gloves of a person.

The light emission sources 102a, 102b, 102c may flash intermittently or may be a constant beam of ultraviolet light depending on the concentration of pathogen load in an area or on the battery concerns. For example, in a hospital where pathogen loads are high in the air, a person may desire to have the light emission sources 102a, 102b, 102c at constant emission to inactivate the many pathogens that are inevitably floating in a hospital full of infected patients. On the other hand, to conserve power of a battery of the power source 112, the light emission sources 102a, 102b, 102c may flash at any interval time sufficient to inactivate floating pathogens in a space. For example, the interval time may be about 0.1 seconds or more, 0.3 seconds or more, or about 0.5 seconds or more, The interval time may be about 1.0 seconds or less, about 0.8 seconds or less, or about 0.7 seconds or less.

The light emission sources 102a, 102b, 102c may include a filtering technique on or inside bulbs or lenses of the light emission sources 102a, 102b, 102c to target any wavelength of ultraviolet light between about 190 nm and 225 nm and remove any undesired ultraviolet light wavelengths. The filter may be chosen so that the light emission sources 102a, 102b, 102c with a significantly broad wavelength range can be used, and the undesired wavelengths across that range are removed by the filter. The filter may be a chemical or dielectric coating. The filter may be a gas trapped within the bulbs or the lenses of the light emission sources 102a, 102b, 102c that blocks certain ultraviolet wavelengths from exiting the bulbs or the lenses. For example, if the light emission sources 102a, 102b, 102c use a component to emit light at a wavelength of about 200 nm to about 400 nm, a filter can be applied to bulbs or lenses of the light emission sources 102a, 102b, 102c to narrow the wavelength emitted in front a face of person to about 190 nm to about 225 nm or narrower, such as about 207 nm to about 222 nm. With this approach, the light emission sources 102a, 102b, 102c could use widely available components in combination with a filter on the bulbs or lenses to provide wavelengths that inactivate the pathogens and do not damage tissue of a human.

The eyeglass device 100 and methods thereof are effective at killing or inactivating one or more microbiological organisms caught in the beam of ultraviolet light. In many instances, the microbiological organisms can include one or more pathogens that are airborne. Non-limiting examples of pathogens that can be inactivated by the beam of ultraviolet light may include one or more various gram positive bacteria such as *Citrobacter freundii, Citrobacter diversus, Corynebacterium diptheriae, Diplococcus pneumoniae, Micrococcus* sp. (I), *Micrococcus* sp. (II), *Micrococcus* sp. (III), *Mycobacterium* spp., *Staphylococcus albus, Staphylococcus aureus, Staphylococcus citrens, Staphylococcus epidermidis, Streptococcus faecalis, Streptococcus pyogenes*. Non-limiting examples include gram negative bacteria such as *Acinetobacter calcoaceticus, Enterobacter aerogenes,*

*Enterobacter aglomerans* (I), *Enterobacter aglomerans* (II), *Escherichia coli, Klebsiella pneumoniae, Nisseria gonorrhoeae, Proteus mirabilis, Proteus morganii, Proteus vulgaris, Providencia* spp., *Pseudomonas, Pseudomonas aeruginosa, Pseudomonas fragi, Salmonella choleraesuis, Salmonella enteritidis, Salmonella gallinarum, Salmonella gallinarum, Salmonella schottmuelleri, Salmonella typhimurium, Salmonella typhosa, Serratia marcescens, Shigella flexnerie* Type II, *Shigella sonnei*, and/or *Virbrio cholerae.*

The eyeglass device 100 and methods thereof as disclosed herein are also effective in eliminating and preventing the re-inoculation of viruses in front of the face of a person. Non-limiting examples of viruses that can be reduced or eliminated by coverage of the beam of ultraviolet light as disclosed herein may include Coronaviridea including the subfamily Orthocoronavirinae (such as beta coronaviruses like SARS-CoV, SARS-CoV-2, MERS-CoV), as well as Adenovirus Type IV, Feline Pneumonitis, Herpes Simplex Type I & II, HIV-1 (AIDS), Influenza A virus, Influenza B virus, Poliovirus, and/or Reovirus.

The beam of ultraviolet light may also be effective against molds and fungi, and non-limiting examples of which are the following: *Altemaria altemata, Aspergillus niger, Aureobasidium pullulans, Candida albicans, Cladosporium cladosporioides, Drechslera australiensis, Gliomastix cerealis, Microsporum audouinii, Monilia grisea, Phoma fimeti, Pithomyces chartarum, Scolecobasidium humicola, Trychophyton interdigitale*, and/or *Trychophyton mentagrophytes.*

Any of the pathogens discussed herein may have any form sufficient to become airborne and subsequently float towards a face of a person. For example, the pathogens may be in a droplet or particle form that can have the ability to float in ambient air. In some pathogens, once forced into an airborne form, the pathogen may remain suspended in air for a long period of time by being on dust particles, respiratory droplets, and/or water droplets. In the airborne form, the pathogens may be light enough to be easily inhaled when floating proximate to the face of a person. In addition, the pathogen may be in a form that is not airborne until a person exhales and forces out droplets of airborne pathogens from the mouth into the ambient air, which presents a risk of infection from non-infected persons inhaling the droplets. For example, the exhalation may be coughing, sneezing, laughing, exercising, or the like. The pathogens in an aerosol or airborne form can travel long distances once exhaled. The distance can be about 3 meters or less, about 2 meters or less, or about 1 meter or less. The distance can be about 0.25 meters or more, about 0.5 meters or more, or about 0.75 meters or more.

The eyeglass device 100 and method disclosed herein can deactivate the pathogens entrained in the various areas in front of the face of a person. The beam of ultraviolet light activates over the pathogen and the pathogens caught in the light kills pathogenic material without damaging any human tissue that is also caught by the beam of ultraviolet light. The pathogen may be killed by denaturing the target pathogenic material by denaturing lysing cellular material in the case of bacterial pathogens, denaturing the lipid envelop in the case of viral pathogens, etc. Killing or denaturing the pathogens caught in the beam of ultraviolet light renders the pathogens inert and stops transmission and contraction of active infectious diseases by inhalation or contact with the eyes or other mucous containing organs.

In the eyeglass device 100 and method as disclosed herein, the beam of ultraviolet light can be activated and directed over a pathogen that is airborne for a time sufficient to reduce or eliminate the pathogen load associated with the space in front of a face of a person. For example, the time to inactivate the pathogen may be upon instant contact with the beam of ultraviolet light. In other examples, the time to inactivate the pathogen may be about 0.5 seconds or more, about 1 second or more, or about 5 seconds or more. The time to inactive the pathogen may be about 30 seconds or less, about 15 seconds or less, or about 10 seconds or less.

The disclosure herein further provides a method for inactivating a pathogen using one or more eyeglass devices 100 described herein. One eyeglass device 100 may be used to protect a single person from coming into contact with active pathogen, or a combination of eyeglass devices 100 may be used to prevent transmission from an infected person that is transmitting the pathogen in an aerosol form.

Where a single eyeglass device is used, the eyeglass device 100 is used by securing the eyeglass device 100 to a head of a person so that the eyes, nose, and/or mouth are covered by the lens(es). After securing, the light emission sources 102a, 102b, 102c are activated so that a beam of ultraviolet light is emitted in front of the face of the person. As the beam of ultraviolet light is emitted in front of the face of the person, any pathogen that is floating in front of the person along a predetermined distance for a period of time would be caught and inactivated by the beam. With this approach, a person wearing an eyeglass device 100 could freely walk around a building or outside where pathogens may be floating in an aerosol form, and the eyeglass device 100 would inactivate the pathogens before reaching the nose, mouth, or eyes of the person wearing the eyeglass device 100.

In methods where multiple eyeglass devices 100 are used, two or more non-infected persons may secure the eyeglass device 100 to a head of each person so that the eyes, nose, and/or mouth of each person are covered by the lens(es). After securing, the eyeglass devices 100 may be activated to emit the beam of ultraviolet light from the light emission sources 102a, 102b, 102c. When the eyeglass devices 100 are emitting beams of ultraviolet light, the two or more non-infected persons may enter the room of an infected patient and perform a procedure without the risk of contracting the infection from the infected patient coughing, speaking, or generally breathing, which can cause the infected person to exhale a pathogen in an aerosol or airborne form.

Additionally, where one or more eyeglass devices 100 are used, a person can adjust the angle of the beam of light emitted from the eyeglass device 100 so that the nose, eyes, and/or mouth of a person are more effectively covered by the beam(s) of ultraviolet light. The angle can be adjusted by any known method, such as by rotating the light emission sources 102a, 102b, 102c. To control emission of the beam to other people or spaces farther or closer than desired, a person may adjust the light emission sources 102a, 102b, 102c to reduce or increase the strength of the beam of ultraviolet light by tapping a button, such as the switch 114, so that a more desirable space is covered by the beam and, subsequently, pathogens are inactivated in that desired space. To change the amount of power being used, a person may change whether the light emission source 102a, 102b, 102c, emits an intermittently flashing or constant beam as described previously. As an extra precaution, a person may apply a face covering or other PPE to prevent contact of active pathogen that is not caught by the beam of ultraviolet light.

Accordingly, using the eyewear or eyeglass devices 100 and/or the method described herein, a person may inactivate a pathogen by shining the beam of ultraviolet light over the pathogen, and the beam of ultraviolet light does not damage the tissue of the person at the desired wavelength.

While the disclosure has been described in connection with certain examples, it is to be understood that the disclosure is not to be limited to the disclosed examples but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. An eyeglass device for inactivating a pathogen, comprising:
    a frame connectable with a face of a person;
    one or more lenses connected with the frame; and
    a light emission source connected to the frame and configured to emit an ultraviolet light beam having a wavelength of about 190 nm to about 225 nm.

2. The eyeglass device of claim 1, wherein the light emission source does not emit an ultraviolet light beam having a wavelength of about 250 nm or more.

3. The eyeglass device of claim 1, wherein the light emission source is configured to emit an ultraviolet light beam having a wavelength of only about 207 nm to about 222 nm.

4. The eyeglass device of claim 1, wherein the light emission source is configured to emit an ultraviolet light beam having a wavelength of about 222 nm.

5. The eyeglass device of claim 1, wherein the one or more lenses include a composition to protect eyes of the person against ultraviolet light damage.

6. The eyeglass device of claim 1, wherein the eyeglass device is a face shield, goggles, or eyeglasses, and wherein the light emission source is affixed to a bridge of the face shield, goggles, or eyeglasses.

7. The eyeglass device of claim 1, wherein the light emission source includes at least two light sources each affixed to one or more of temples, a bridge, or rims of the frame.

8. The eyeglass device of claim 1, wherein the light emission source is positioned on the frame to emit the ultraviolet light beam at a downward angle of about 10 degrees to about 85 degrees.

9. The eyeglass device of claim 1, further comprising:
    a battery connected with the light emission source and configured to provide energy to the light emission source.

10. A method of inactivating a pathogen comprising:
    securing an eyeglass device connected with a light emission source at a frame of the eyeglass device, wherein eyes of a person are covered by one or more lenses of the frame, and wherein the light emission source is configured to direct ultraviolet light away from a face of the person;
    activating the light emission source of the eyeglass device so that the ultraviolet light is emitted, the ultraviolet light having a wavelength between about 190 nm and about 225 nm; and
    inactivating the pathogen having a form of an aerosol droplet that is floating in front of the face of the person.

11. The method of claim 10, wherein the light emission source of the eyeglass device is positioned to direct light at a downward angle of about 85 degrees to about 25 degrees.

12. The method of claim 10, wherein the light emission source of the eyeglass device is positioned to direct light at a downward angle below about 75 degrees.

13. The method of claim 10, further comprising:
    flashing the light emission source of the eyeglass device intermittently.

14. The method of claim 10, wherein inactivating the pathogen having the form of the aerosol droplet that is floating in front of the face of the person includes denaturing the pathogen so that the pathogen is no longer infectious.

15. The method of claim 10, wherein the one or more lenses include a composition that blocks some wavelengths of beams of ultraviolet light so that ultraviolet light does not reach the eyes of the person.

16. Eyeglasses for inactivating a pathogen, comprising:
    an eyeglass frame connectable with a face of a person;
    a pair of lenses connected with the eyeglass frame, the pair of lenses including a composition that blocks some wavelengths of beams of ultraviolet light; and
    a light source affixed to the eyeglass frame and configured to emit an ultraviolet light beam having a wavelength of about 205 nm to about 225 nm and not configured to emit an ultraviolet light beam having a wavelength of about 254 nm.

17. The eyeglasses of claim 16, wherein the light source is configured to emit an ultraviolet light beam having a wavelength of about 222 nm.

18. The eyeglasses of claim 16, wherein the light source comprises multiple light sources respectively affixed to the eyeglass frame at a bridge or a temple of the eyeglass frame.

19. The eyeglasses of claim 16, wherein the light source is affixed to the eyeglass frame at a position to direct light at a generally downward angle so that, when worn by a person, the ultraviolet light beam is directed to a location in front of and proximate to at least one of a nose; or a mouth of a person.

20. The eyeglasses of claim 16, wherein the light source is affixed to the eyeglass frame at a position to direct light at a downward angle of about 85 degrees to about 25 degrees.

* * * * *